(12) United States Patent
Kincaid et al.

(10) Patent No.: US 7,930,108 B2
(45) Date of Patent: Apr. 19, 2011

(54) EXPLORATORY VISUALIZATION OF PROTEIN COMPLEXES BY MOLECULAR WEIGHT

(75) Inventors: Robert H. Kincaid, Half Moon Bay, CA (US); Rudolf Grimm, Campbell, CA (US); Patrick D. Perkins, Sunnyvale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 471 days.

(21) Appl. No.: 12/011,347

(22) Filed: Jan. 25, 2008

(65) Prior Publication Data

US 2009/0192719 A1 Jul. 30, 2009

(51) Int. Cl.
*G06F 19/00* (2006.01)
(52) U.S. Cl. ........................................ 702/19
(58) Field of Classification Search .................. 702/19, 702/182–185; 436/86
See application file for complete search history.

(56) References Cited

U.S. PATENT DOCUMENTS

| | | | |
|---|---|---|---|
| 2008/0096284 A1* | 4/2008 | Lubman et al. | 436/86 |
| 2009/0021517 A1* | 1/2009 | Foslien | 345/440 |
| 2009/0093971 A1* | 4/2009 | Barrett et al. | 702/22 |

OTHER PUBLICATIONS

Andersen et al., Proteomic characterization of the human centrosome by protein correction profiling, pp. 570-574, vol. 426, Dec. 2003.
Camacho et al., Two-dimensional Blue Native/SDS Gel Electrophoresis of Multi-Protein Complexes from Whole Cellular Lysates, pp. 176-182, 2004.
Foster et al., A Mammalian Organelle Map by Protein Correlation Profiling, pp. 187-199, Apr. 2006.
Huber et al., Organelle Proteomics: Implications for Subcellular Fractionation in Proteomics, pp. 962-968, 2003.
Kincaid et al., ProteoVis: An Analysis Platform for Multidimensional Protein Separations, 1 pg., Feb. 2006.
Tan et al., High-Throughput localization of organelle proteins by mass spectrometry: a quantum leap for cell biology, pp. 780-784, 2006.

* cited by examiner

Primary Examiner — Edward Raymond

(57) ABSTRACT

Methods, user interfaces, systems and computer readable media for visualizing data to facilitate analysis of the data. Mass data values are provided for a sample having been separated into portions according to a first characteristic of the sample, the slices having been processed to provide the mass data values of members of the sample occurring in the portions. A plot of the mass data values is displayed on a first axis versus the portions on a second axis of the plot. A mass data value of a member may be selected on the plot, and all mass data values occurring in the portion in which the selected mass data value is located are displayed using first visual indicators that are visibly distinct from visual indicators used to display data values occurring outside of the portion in which the selected data value is located.

30 Claims, 10 Drawing Sheets
(8 of 10 Drawing Sheet(s) Filed in Color)

US 7,930,108 B2

EXPLORATORY VISUALIZATION OF PROTEIN COMPLEXES BY MOLECULAR WEIGHT

BACKGROUND OF THE INVENTION

The analysis of proteins and protein complexes in an effort to understand functions of proteins in a biological organism is complex and unwieldy. Some efforts have been made to separate protein complexes using one or two-dimensional separation methods, such as gel electrophoresis methods. Complexes of proteins are moved through the gel or other separation medium as intact entities (either as native interacting complexes, or covalently bound using chemical reagants). Once separated portions of the gel or medium can be further analyzed to determine the protein constituents of isolated complexes. For example, mass spectrometry and/or liquid chromatography techniques may be employed to identify the protein constituents of a complex.

Proteins identified within a portion can be inferred to be putative members of the same protein complex. Inferences about signaling may also be inferred where one or more proteins are present in a complex in one sample, but are absent from that complex in another sample, for example. However, comparisons between such samples are often difficult to perform with existing technology, and are often performed manually.

It would also be useful to provide a way to interrogate and or compare proteins that are existent in portions of the same sample, as the same protein may be found interacting in different protein complexes of the sample, and/or provide some clue about cell function signaling etc., when such comparisons are made. Again, this is currently very cumbersome to do, often requiring manual review of results from the different portions in an effort to make such comparisons.

Accordingly, there is a need for systems and methods for rapid examination of protein complex data sets to facilitate researchers understanding of functions of and interactions between constituents of the complex datasets.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
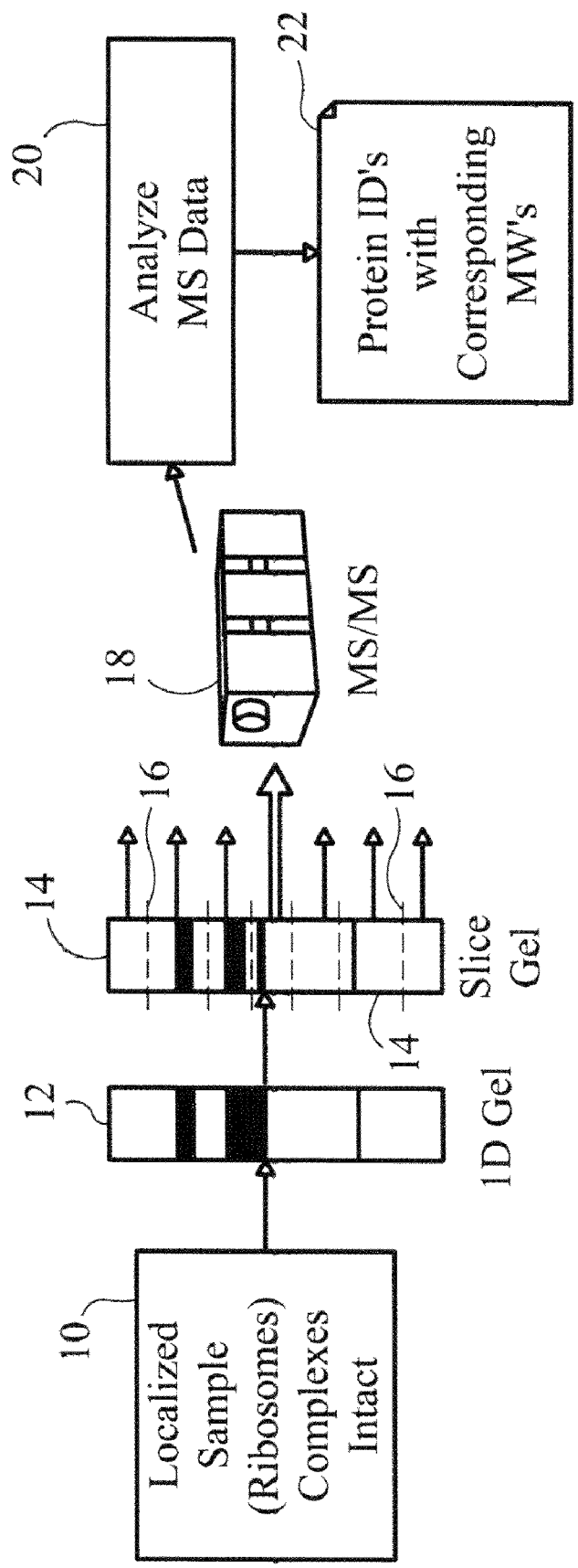
FIG. 1 is a schematic illustration of one example of a method for providing molecular weight data for protein complexes in a sample, as well as molecular weight data for individual proteins.

Before the present methods, systems and computer readable media are described, it is to be understood that this invention is not limited to particular separation processes, mass spectrometry processes or other separation processes described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a visual indicator" includes a plurality of such visual indicators and reference to "the plot" includes reference to one or more plots and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

A "protein complex" or "complex" refers to a group of two or more associated proteins formed by protein-protein interaction. Protein complexes are a form of quaternary structure.

The term "portion", as used herein in connection with a sample, refers to a slice, fraction, bin, sub-sample or other term used to refer to an amount of the sample that is less than the whole sample. The term "slice" is used specifically herein to refer a slice of a protein-containing gel providing a subsample of the proteins contained within the gel. Examples of slices include, but are not limited to liquid chromatography fractions, sediment pellets resulting from different centrifugation steps, etc.

The present invention permits rapid examination of a protein complex dataset in a way that shows multiple conceptual angles to data of interest as the data is selected. For example, a single mouse click on data of interest can simultaneously reveal several different relationships in which the data of interest participates. This enhances and expedites the exploratory examination of the data by a user.

The present invention provides unique and novel associations of data by associating the molecular weight of a complex with the molecular weights of the proteins making up that complex. The two-dimensional display of these two attributes along with linked details and other custom user interface elements provide effective and novel ways to view, manipulate and explore the data.

Referring now to FIG. 1, one example of a method for providing molecular weight data for protein complexes in a sample, as well as molecular weight data for individual proteins is schematically illustrated. In this example, a biological sample 10 is provided from a biological source, and cells of the sample are pre-fractionated to enrich the sample for a specific cellular location. For example, the sample 10 in FIG. 1 concentrates on ribosomal complexes, but the process may be performed to concentrate on other specific cellular locations. The enriched sample 10 is kept under conditions that preserve intact the protein complexes (in this example, ribosomal complexes) and is applied to a one-dimensional (1D) gel separation process 12 referred to specifically as a "native gel" process, since the process is carried out under nondenaturing (i.e., "native") conditions, see, e.g., Camacho-Carvajal, "Two-dimensional Blue native/SDS Gel Elecrophoresis of Multi-Protein complexes from Whole Cellular Lysates", Molecular & Cellular Proteomics 3.2, 176-182, 2004, incorporated by reference herein, for a further description of an example of a native gel process performed in two dimensions. The 1-D native gel separation process referred to above allows the separation of the protein complexes from one another, even those with high combined molecular weights. The migration time of a complex through the gel (i.e., gel migration time) is proportional to the molecular weight of the complex.

Slices 14 are formed by slicing 16 the gel 12 into slices 14 as illustrated in FIG. 1. Each slice 14 corresponds to a specific molecular weight range of a particular protein complex. Each slice is then tryptically digested in-gel and further analyzed by mass spectrometry 18 to provide molecular weight data of proteins identified within the slice 14. In the example shown in FIG. 1, tandem mass spectrometry (MS/MS) is employed, although other mass spectrometry processes may be alternatively employed, including, but not limited to single mass spectrometry processes. Further alternatively, further gel separation processes may be used to measure mass values of the proteins. For example, a second gel separation may be performed under denaturing conditions to separate the constituents. The molecular weights of the constituents (e.g., proteins) can then be measured, although not as accurately as with mass spectrometry or tandem mass spectrometry techniques. Also, this further gel process technique is further limited in that it only identifies molecular weights of the constituents and not any other characteristics of the constituents. For some studies however, the ability to determine molecular weights of the constituents may be sufficient. In a further alternative technique, antibody-based identification techniques may be provided to look for known proteins. These known proteins can then be further analyzed according to the techniques described herein, such as to identify putative protein complexes, by analyzing mass values of proteins that potentially make up the putative protein complexes, for example.

The data output from the mass spectrometry analysis 18 is further analyzed by data analysis software tool 20 to identify the specific proteins indicated by the molecular weight data and associate the specific protein identifications (protein IDs) with their corresponding molecular weights. One example of a data analysis software tool 20 that can be used for this analysis is SPECTRUM MILL® MS Proteomics Analysis Workbench (Agilent Technologies, Inc., Santa Clara, Calif.), although other data analysis software tools suitable for this purpose may be substituted. The data analysis software tool 20 outputs 22 the protein IDs with their corresponding molecular weights (MWs). Accordingly, for each gel slice 14, a listing of all proteins contained therein and identified is output or displayed together with their corresponding molecular weights. As noted, each gel slice represents a different range of molecular weights, which correspond to migration time through the gel 12. Since most protein complexes are heavier (larger in molecular weight) than most individual proteins, it is expected that a slice 14 corresponding to the molecular weight of a protein complex would be enriched for complexes and include relatively few single protein entities. Thus it is inferred that proteins that are within the same slice 14 are putative members of the same protein complex.

Figure 2:
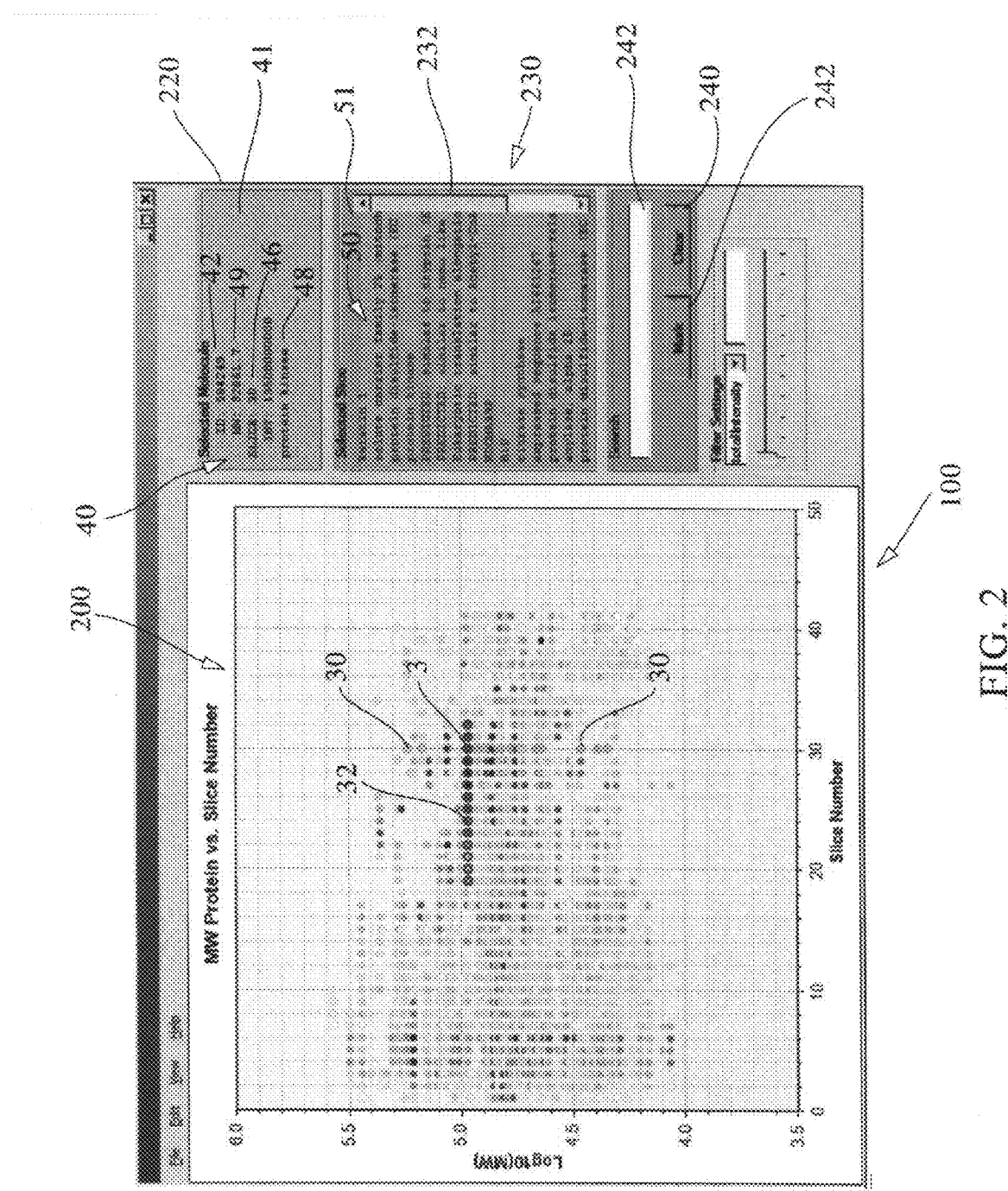
FIG. 2 illustrates a plot having units of the molecular weight data values on a $Log_{10}$ scale along the Y-axis of the plot versus the slice numbers on the X-axis, and wherein a particular mass data value has been selected.

The data resulting from the processing described with regard to FIG. 1 can be plotted in a plot 200 of molecular weight data values of the proteins versus the molecular weight ranges of the slices 14 as illustrated on the display of the user interface 100 shown in FIG. 2. FIG. 2 illustrates a plot having units of the molecular weight data values on a $Log_{10}$ scale along the Y-axis of the plot 200 versus the slice numbers on the X-axis. The $Log_{10}$ scale is optional, as a linear (or other log) scale could be employed, but the log scale keeps the plot 200 display compact and evenly distributed across a wide range of molecular weights. As noted, each individual slice 14 represents a different range of molecular weights, so the X-axis could alternatively indicate the molecular weight ranges against which the molecular weights of the proteins are plotted. Accordingly, the molecular weight data values are plotted as molecular weights of the proteins (Y-Axis) versus molecular weights of the protein complexes (X-axis).

The output 22 resulting from the analysis of the mass spectrometry data is typically a large spreadsheet of protein identifications and their corresponding molecular weights and possibly some information about from which slice the protein molecular weight data originated. This format is not user-friendly and not conducive to analyzing protein complex make-ups, or to facilitating exploration and understanding of the protein complexes, proteins that form them or other related knowledge. By plotting the molecular weights of the proteins versus slice number or molecular weights of the protein complexes, as illustrated in plot 200 of the visualization on user interface 100 in FIG. 2, the groupings of the proteins in each slice can be readily visualized by a user, making it much simpler to identify and explore putative protein members of a protein complex. The present invention is further provided with additional features that further facilitate the ease of visually identifying and exploring proteins that may be members of a protein complex, as well as other locations that such proteins may be found in the sample.

FIG. 2 illustrates an instance where a protein is selected by selecting its molecular weight data value 3 by a user of user interface 100, such as by mouse click, keystroke or other selection mechanism. Upon making this selection, all of the molecular weight data values occurring in the particular slice that the selected value 3 is found in are then indicated with using a first type of visual indicator 30 (such as highlighting them in gold, as in FIG. 2), and all occurrences of the protein with the selected molecular weight data value are indicated with a second type of visual indicator 32 (such as highlighted in blue, as in FIG. 2) that is visually distinct from the first type of visual indicator 30. All other molecular weight (mass) data values are displayed with a third type of visual indicator that is visually distinct from the first and second types of visual indicators. In the example shown in FIG. 2, all other mass data values are shown in gray scale. In the example of FIG. 2, the blue circles 32 all appear adjacent to one another and a user might conclude that this represents a difficult separation of the complex to which the selected protein belongs and that the complex therefore appears in more than one consecutive slice 14. In other instances, blue circles may be widely separated in the display of the plot 200, which might indicate that the selected protein is participating in more than one complex.

Additionally, a pane 220 (captioned "Selected Molecule" in FIG. 2) is displayed on the user interface 100 that displays metadata 40 characterizing the molecule that the selected mass data value 3 represents. Metadata 40 that can be displayed include, but are not limited to: protein ID 42, molecular weight 44, slice number 46, molecular weight range represented by the slice (not shown), protein name 48, etc. Additionally, at least a portion of the pane 220 can be color-coded 41 to match the visual indicator representing the selected mass data value 3. In the example of FIG. 2, pane 40 is colored coded 41 blue to match the blue color coding of the selected mass data values representing the selected protein 3 in other slices, each of which mass data values 32 are also color coded blue.

Additionally, user interface 100 may display a pane 230 (captioned "Selected Slice" in FIG. 2) in which metadata characterizations 50 of all mass data values 30 occurring in the slice that the selected mass data value 3 occurs in are displayed. As noted, these mass data values represent possible members of the complex or complexes found in that slice. In the example shown, pane 230 displays the protein names of all the proteins represented by the mass data values 30 occurring in the slice of the selected mass data value 3. Alternatively or additionally, other metadata characterizations 50 may be displayed, including, but not limited to, protein ID and/or molecular weight. Additionally, at least a portion of the pane 230 can be color-coded 51 to match the visual indicator representing the mass data values 30. In the example of FIG. 2, pane 230 is colored coded 51 gold to match the gold color coding of the mass data values 30 in the slice in which the selected mass data value 3 occurs, and each of the mass data values 30 are also color coded gold.

Thus, a single mouse click or other single selection action by a user of user interface 100 on the display 200 provides a considerable amount of immediate information, with very little effort by the user. The results are displayed virtually instantaneously, thus facilitating rapid browsing of the data for studying molecules of slices of interest. A slider or other navigation feature 232 may be provided in panel 230 to facilitate changing the information that is displayed in panel 230. This is particularly useful when there are more mass data values in a selected slice than can all be displayed in the pane 230 at the same time.

Clicking on or otherwise selecting a protein in the panel 230 inserts the string representing the selected protein into a search mechanism 240 for use in a manner described in greater detail below with regard to search mechanism 240. Alternatively, the panel 230 may be configured so that clicking on or otherwise selecting a protein in panel 230 causes the selection of the protein of interest 3 to be changed to the selected protein and displayed as such in plot 200.

To aid in finding molecules of interest, a search mechanism 240 may also be provided on user interface 100. A search string can be entered by a user into the box 242, after which the user can either press the enter key on the keyboard of the computer system provided with the user interface 100 or mouse click on or otherwise select the "Mark" button 242 provided on the search mechanism pane 240. These actions cause all mass data values having characteristics matching the search string to be identified with a visual indicator that is distinct from all visual indications of mass data values that do not have characteristics matching the search string.

Figure 3:
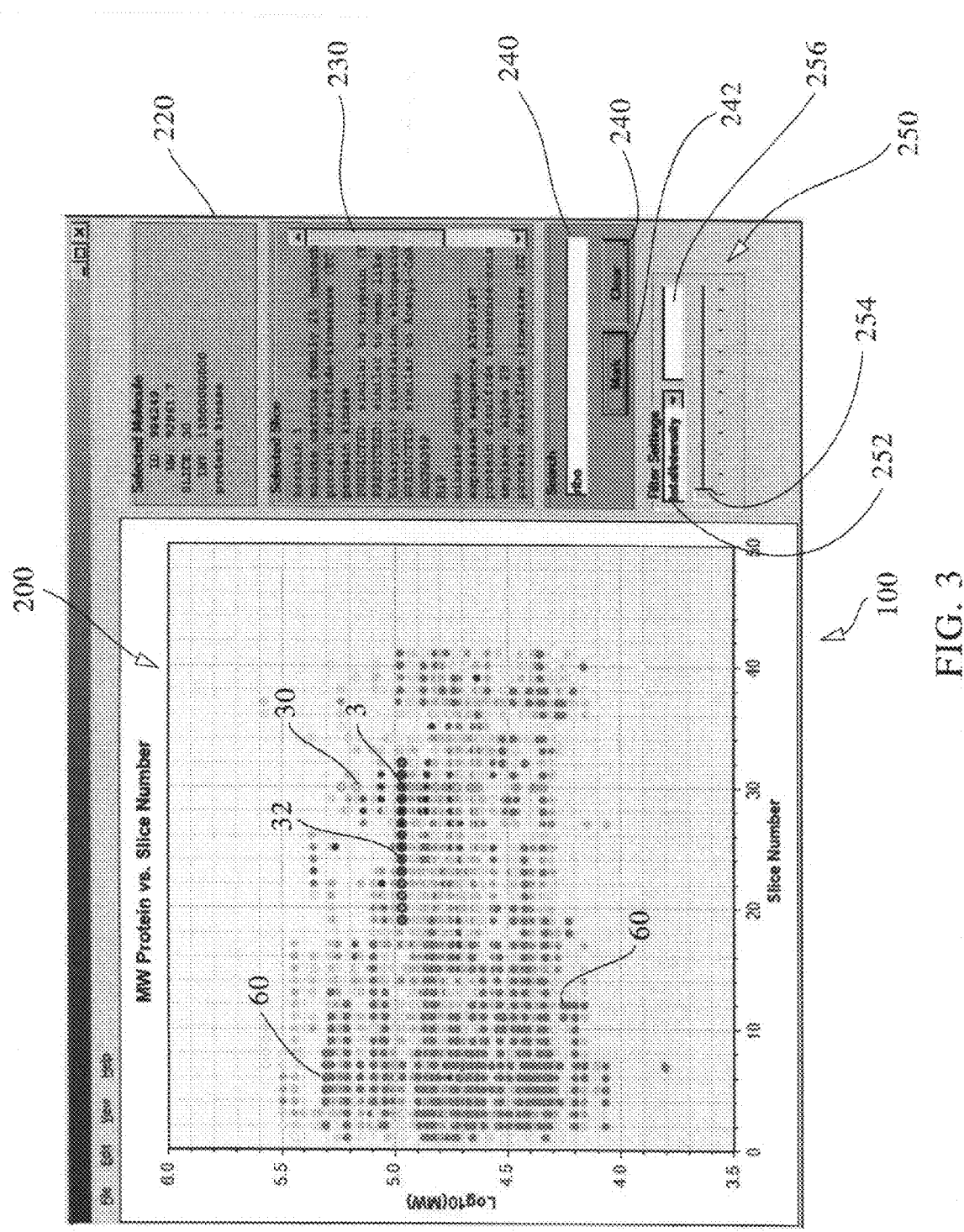
FIG. 3 illustrates an example of the use of the search mechanism of the user interface shown in FIG. 2.

FIG. 3 illustrates an example of the use of the search mechanism 240 in which the user has entered the search term "ribo". The mass data and metadata associated with the mass data are searched to find matches with the search term, and then all mass data values displayed on plot 200 that include a match (either the mass data value itself, or at least one occurrence of metadata associated with that mass data value) with the search term are displayed with the unique visual indicator, as noted above. In the example shown in FIG. 3, all mass data values found to match are displayed with red color coding. Additionally, at least a portion of the pane 240 can be color-coded 241 to match the visual indicator representing the mass data values 60. In the example of FIG. 3, pane 240 is colored coded 241 red to match the red color coding of the mass data values 60 matching the search term. The effect of this example was to identify all proteins related to ribosomes. This search feature 240 provides a quick and easy way of a user to find all instances of a class of proteins in the sample.

More complex searching schemes may also be carried out. For example, if Gene Ontology annotations are associated with the mass data values as part of the metadata characterizations, then precise searches by cellular location, biological function, or biological processes can be performed. Other types of annotation, such as pathway membership may also be provided as metadata characterizations and can also be searched.

Various methods of filtering the display 200 can also be performed. User interface 100 may be provided with a filtering mechanism 250 such as the combo box shown in FIG. 3. Combo box filtering mechanism 250 may include a drop down menu 252 from which a user may select a criterion by which to filter. The filtering mechanism may be provided with a default criterion, such as "total intensity" in the example shown in FIG. 3. Independent of any filtering, this criterion is used for the default color of the mass data values that are not otherwise color coded by a visual indicator. Thus, those mass data values not actively selected in some fashion are shown in various shades of gray. The gray scale gradient used to shade these mass data values is linearly proportional to the criterion selected. Thus, in the case where "total intensity" is the criterion, as shown in FIG. 3, the darkest gray mass data values are those with the highest total intensity, while the faintly shaded mass data values have relatively low reported total intensity. "Total intensity" is used here in the same manner as that defined by SPECTRUM MILL® MS Proteomics Analysis Workbench, i.e., "extracted ion chromatogram (EIC) of the precursor ion, used for peptide quantitation. The EIC is calculated as the sum of precursor m/z abundance in the MS scans (~chromatographic peak area), and is dependent upon the user-designated scan tolerance (chromatographic time in seconds), the putative precursor m/z (as adjusted by user designation of Find precursor $^{12}$C) and the user-designated mass tolerance for merging scans with the same precursor m/z."

Figure 4:
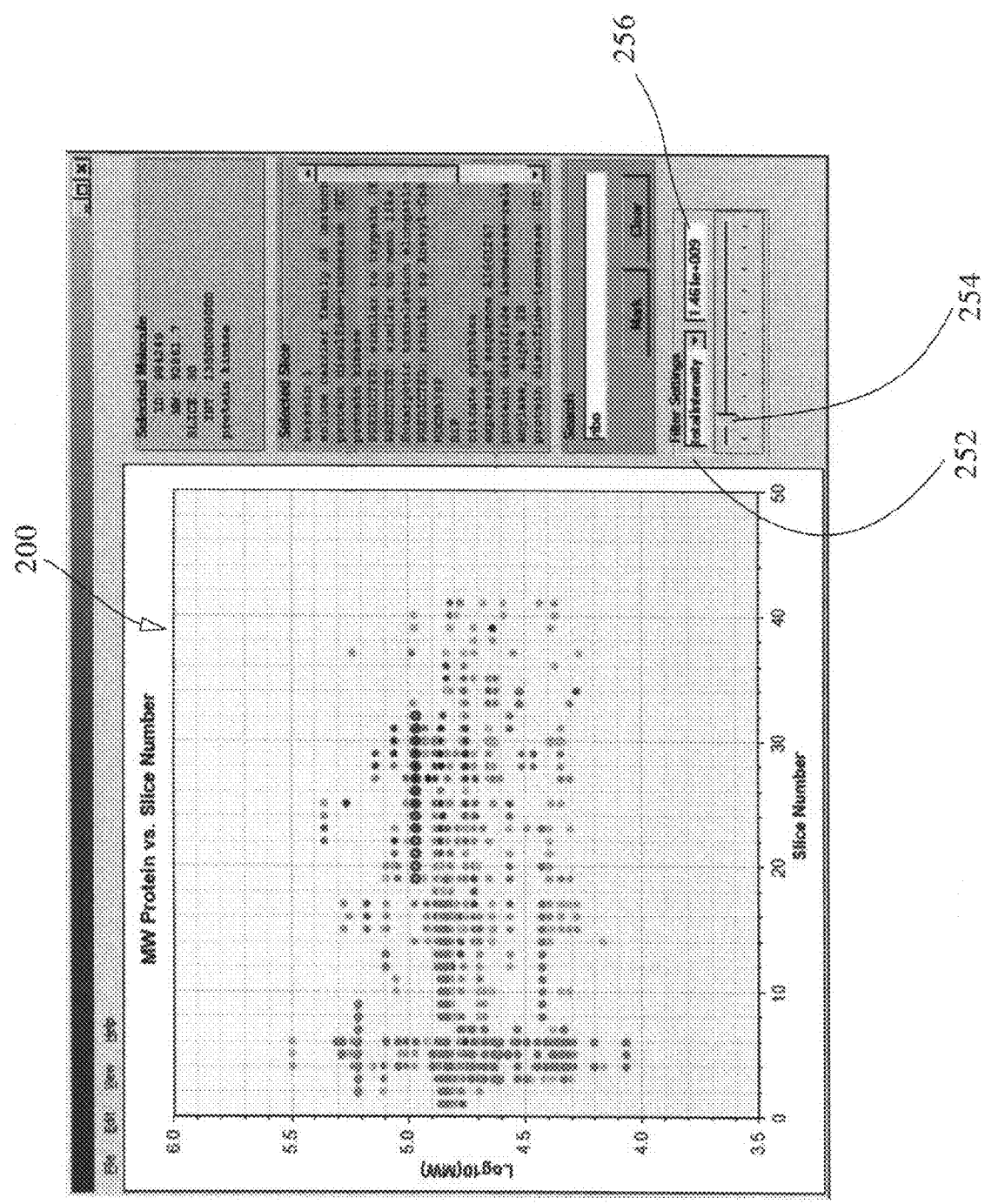
FIG. 4 illustrates an example of a filtering mechanism of the user interface shown in FIG. 2.

The system defaults to displaying all mass data points on display 200, as shown in FIG. 3, regardless of the criterion selected in the menu 252. However, by adjusting the slider 254 or directly entering a limit value in box 256, a limit value is entered by which the mass data values are filtered according to the entered limit or cutoff value. Accordingly, any mass data values having an attribute value below the entered limit value will be filtered from the display 200 and thus not shown on the display 200. FIG. 4 illustrates an example in which the filtering criterion 252 is "total intensity" and a cutoff value of 1.461 e+009 has been entered, either by directly entering it into box 256, or by adjusting slider 254 until that value is displayed in box 256. By comparing the display 200 of FIG. 4 with the display 200 of FIG. 3, it is readily apparent that fewer mass data values are displayed in the display 200 of FIG. 4, after filtering those displayed in the display 200 of FIG. 3.

Figure 5:
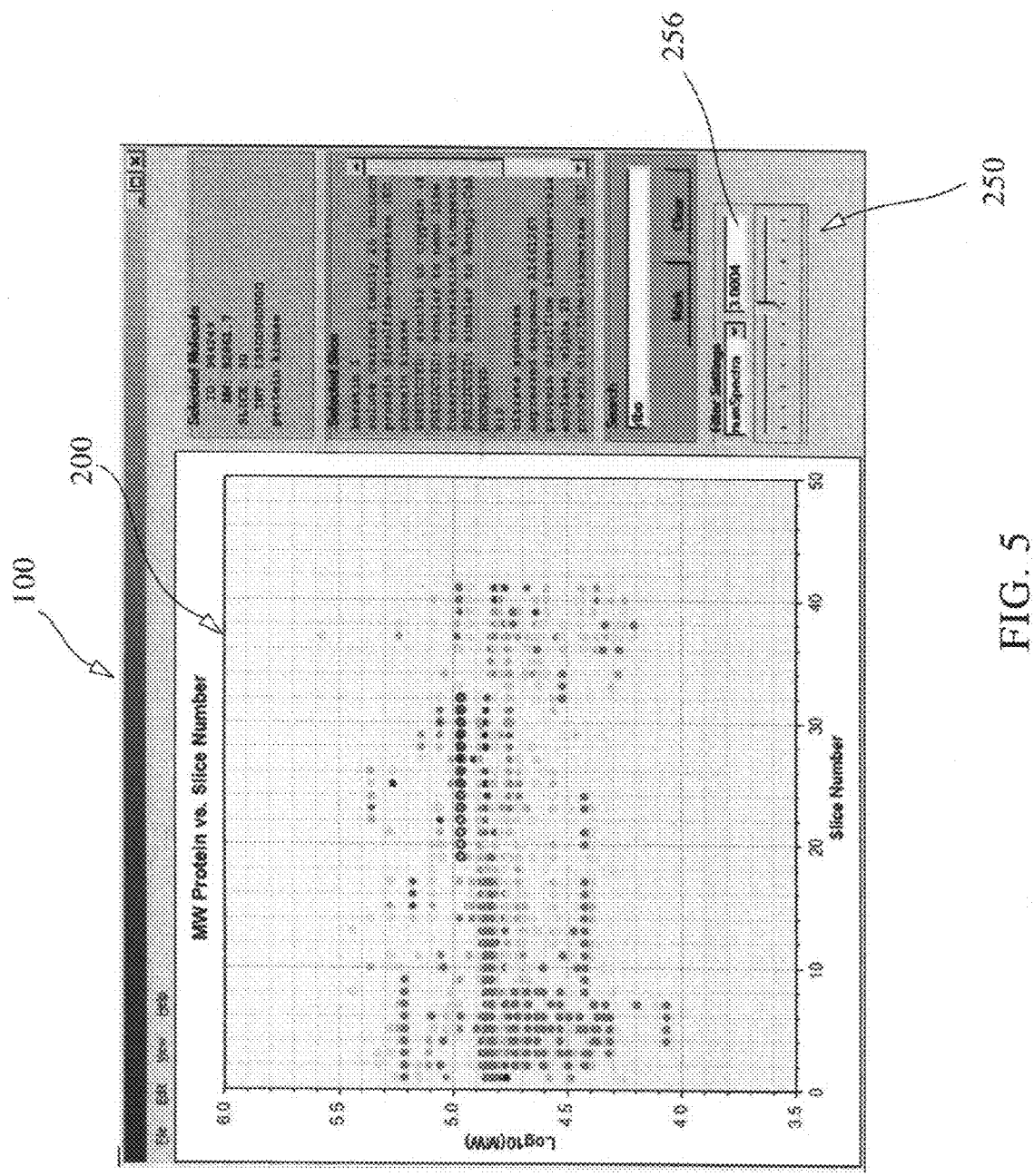
FIG. 5 illustrates another example of a filtering mechanism of the user interface shown in FIG. 2.

FIG. 5 illustrates another example, in which the filtering criterion selected in menu 252 is "numSpectra". In this case, the system filters out mass data values that are associated with the number of spectra being considered by the analysis software at 20 (FIG. 1) less than the specified cutoff number. In the example shown in FIG. 5, the cutoff limit is 3.0004. Other additional or alternative filtering criteria may be used, including any attributes or metadata that are provided and associated with the mass data values as part of the metadata characterizations. A simple example involves simply filtering by molecular weight or mass in order to view only those molecules in a specified molecular weight range. This type of filtering can be used as a measure of confidence, to identify and discount masses from which only one spectrum was obtained. Filtering can be performed based on confidence scores that have been provided by Spectrum Mill software, or alternative software and/or instrument that provides the mass data values and also calculated confidence scores. Other exemplary filtering criteria include, but are not limited to: percent coverage (i.e., how much of the molecule was observed in the mass spectrometry data), and/or essentially any other metadata that can be mapped to a protein mass, such as Gene Ontology annotations, organism identification data, independent experimental measures, etc.

The filtering mechanism 250 of the user interface 100 can thus be used to simplify a complex display 200 by removing those mass data values that a user might believe to be untrustworthy or of little informational value for the purpose at hand. It is further noted that, although not shown, the user interface 100 could readily be configured so that multiple filtering criteria could be selected upon which to set cutoff values to filter the mass data values according to each at the same time.

Figure 6:
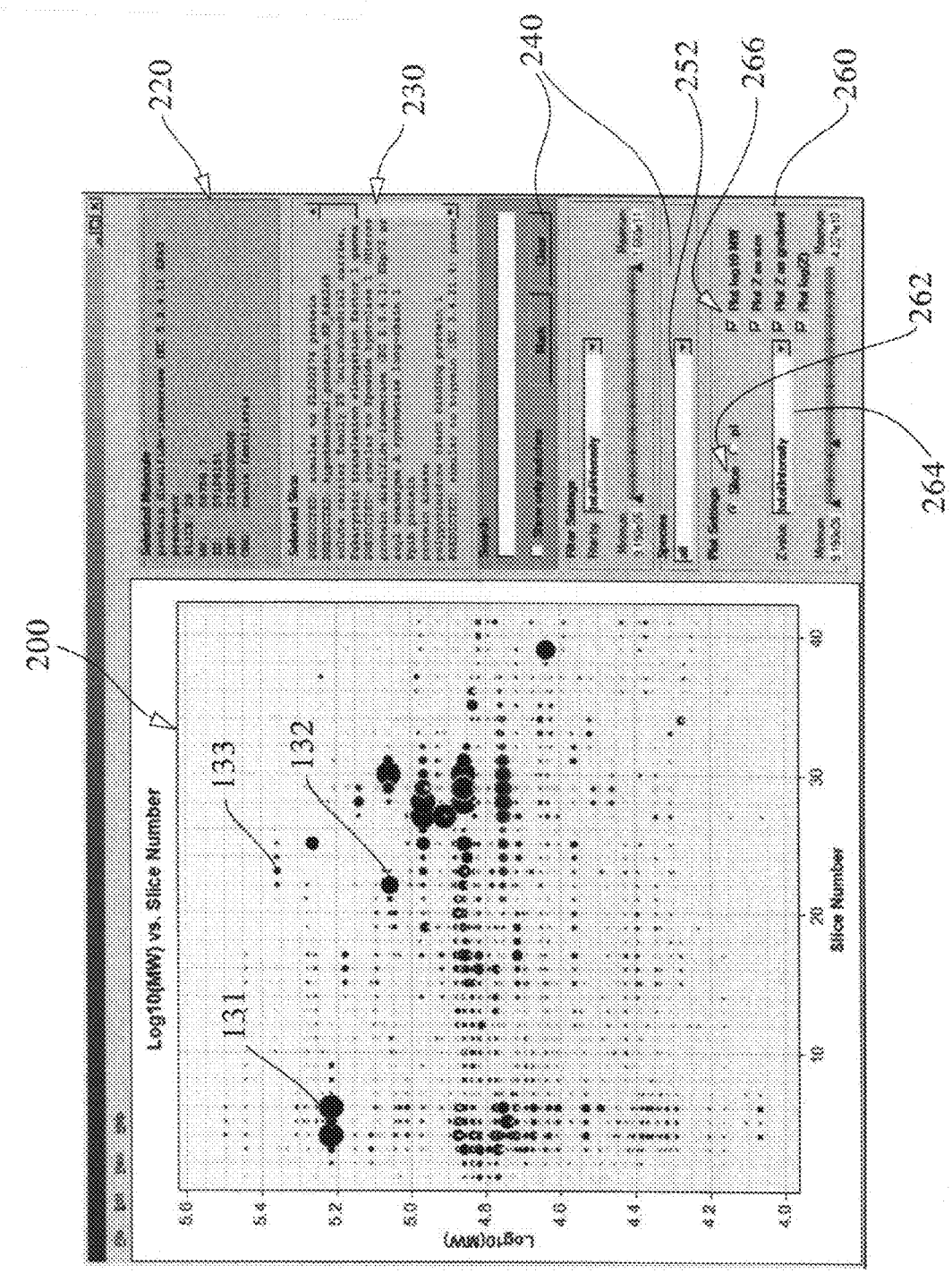
FIG. 6 illustrates varying the indicators representing the mass data values of the plot according to intensity values.

A third attribute of the mass data values (in addition to molecular weight on the Y-axis and slice number or molecular weight range on the X-axis) can be plotted on the display by varying the indicators representing the mass data values. For example, the relative intensities of the mass data values can be displayed by varying the sizes of the indicators relative to the intensities of the mass data values represented thereby, as illustrated in FIG. 6. A plot settings pane 260 may be provided on the user interface with a Y-axis setting 262 that allows the user to select a plot of molecular weight versus slice (or portion or fraction, as the case may be) or molecular weight versus pI, for example. A drop down menu 264 allows the user to select from a list of predetermined attributes to be plotted in the Z-dimension, wherein Z-dimension values are represented by the relative sizes of the symbols plotted. The application of the present system reads tab-delimited text that requires values for molecular weight, pI and at least one signal column associated with a portion. A number of additional columns of data may be provided to the application from Spectrum Mill software or other software and/or hardware used to provide the mass data values. Further optionally, a user can edit the tab-delimited file to add any other columns of metadata that the user may be interested in displaying or using for further analysis of the data. For filtering, as well as size and gradient display indicators, any numeric attribute corresponding to a column in the data file can be used. Examples of such metadata provided by the Spectrum Mill software include, but are not limited to: "numSpectra" (i.e., the number of spectra associated with that protein ID), and "percentCoverage" (percentage of the full protein sequence covered by the peptides used for the ID of the protein).

In FIG. 6, an instance is illustrated in which the user has selected "slice" for the Y-axis setting, and "total intensity" as the Z-value setting. Further checkboxes 266 may be provided to allow the user to select whether molecular weight or log molecular weight values are plotted in the X-axis, whether the Z-axis values are to be represented by size variations, whether Z is to be plotted as a gradient (e.g., a linear gradient of gray scale shades from white to black, where white represents the minimum value and black represents the maximum value, such as when used to color the plotted indicators that are not otherwise color coded as being members of a selected portion or a selected mass data value, for example) and whether the Z-values are to be plotted as log(Z) values. The same kind of linear mapping technique used with the gradient function is also used to compute the radii of the indicators when "Plot Z as size" is selected. Although the example shown in FIG. 6 performs linear gradient mapping, the present methods and systems are not limited thereto, as other types of gradient mappings may be performed, including, but not limited to sigmoid gradient mapping, logarithmic gradient mapping, polynomial gradient mapping. Further alternatively, discrete mapping can be performed wherein different colors are mapped to different ranges of values.

In the example shown in FIG. 6, all of the checkboxes have been selected. Accordingly, $\log_{10}$ values of the molecular weight data are plotted against slice number, $\log_{10}$ Z-values are plotted by variations in size of the indicators representing the molecular weight values, where the size of the indicators are scaled (linear scaling of the radii, as noted above) to the log of the intensity values of those molecular weights in this case. Thus, for example, the total intensity of the data point represented by the size of indicator 131 is greater than the total intensity of the data point represented by the size of indicator 132, and much greater than the total intensity of the data point represented by the size of indicator 133.

Figure 7:
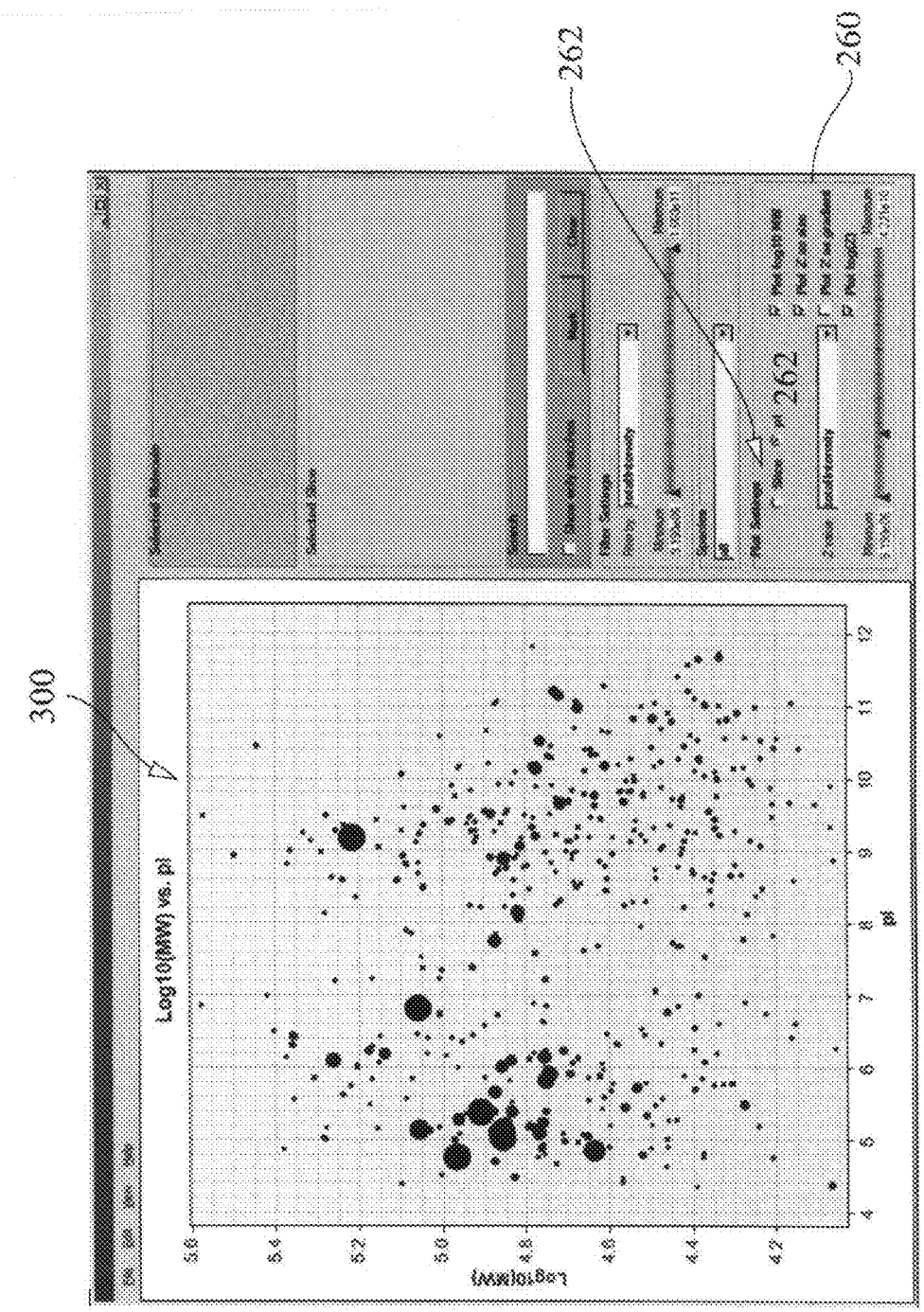
FIG. 7 illustrates a plot having been converted to axes having units of mass data values (molecular weights of individual molecules) vs. pI values of those molecules.

When the metadata characterizations of the mass data values include pI (isoelectric point) values of the mass data values (e.g., included in output 22), a user can operate the user interface 100 to change the plot 200 from a plot of mass data values (molecular weights of individual molecules) vs. slice number/molecular weight range of slices/portions/fractions, to a plot 300 of mass data values (molecular weights of individual molecules) vs. pI values of those molecules as illustrated in FIG. 7. This can be accomplished by selecting "pI" in the X-axis setting feature 262, as shown in FIG. 7. In this example, "Plot Z as gradient" has not been selected. When plotting with the gradient, each instance of the same protein (molecular weight) being plotted will typically have a somewhat different coloring since the intensity of the protein will typically vary across different portions (slices). However, when molecular weight is plotted vs. pI, all the instances of the protein across slices (portions) have the same pI and molecular weight so that they end up being plotted on top of one another. The result is typically a plurality of overlaid grey circles, so it is generally clearer to plot molecular weight vs. pI plots without using the "Plot Z as gradient" feature. Plot 300 includes the same X- and Y-axes dimensions that are used in a plot of results from a two-dimensional (2D) electrophoresis gel process, and so provides a familiar visualization to those that are experienced in working with 2D gels. Accordingly, if the user is familiar with where certain proteins are generally located in 2D gel plots, then the plot 300 facilitates the ease with which the user can readily locate the proteins.

When viewing the mass data values in plot 200, it may be noted that there are similar patterns of occurrences of proteins across contiguous gels. In such cases, this information may be used to form hypotheses about the protein complexes formed by these proteins, as evidenced by the similar pattern of occurrences. Additionally, there may also be one or more proteins that show up in one or more, but not all of the contiguous slices. In this case, there may be a similarity of these occurrences across samples, i.e., when comparing multiple plots 200. These might also then be considered to be putative members of a protein complex, together with the proteins showing the similar contiguous patterns. The system can be configured to compare migration patterns of protein molecules, where a migration pattern is defined by a vector of intensity values of a protein molecule across slices. When the migration patterns of two or more proteins are occurring in at least a predefined number of the same slices and have a similarity value greater than or equal to a predefined similarity threshold minimum value, then these proteins are identified as being putative members of the same protein complex and are displayed on the user interface for review by a user. It should be noted her that intensity can be used as an approximate surrogate measure of protein abundance.

Thus, similarity between protein intensity vectors can be computed using any typical measure of similarity, including, but not limited to Pearson correlation, Euclidean distance, cosine distance, etc. These methods of measuring similarity between vectors are well-known and therefore will not be described in further detail here. The resulting similarity values from the calculation provide a relative measure of how similar the profile for one protein is to that for another. The more similar they are, the more confidently it may be concluded that the similar proteins form a complex.

In cases where molecular weights of proteins are plotted against cellular location, such as by use of sub-cellular fractionation techniques described in more detail below, typical profiles of proteins plotted against sub-cellular fractions may be known from prior experimentation. Some studies have indicated that the profile of protein abundance across sub-cellular fractions is characteristic of the location of that protein in the cell, e.g., see Foster et al., "A Mammalian Organelle Map by Protein Correlation Profiling", Cell 125, 187-199, Apr. 7, 2006, which is incorporated herein, in its entirety, by reference thereto. In such cases, where a characteristic profile of one or more proteins is known, a Chi-square test of a plotted profile can be computed relative to the expected (known) profile, where both are expressed as vectors across sub-cellular fractions. The Chi-square test provides a statistical measure of how likely it is that the protein represented by the plotted profile is the same class (e.g., cellular location, or, in this case, member of a protein complex) as the protein represented by the known profile. Thus, the system can be calibrated on some known data sets to observe what values are generated from the known datasets. By exercising the algorithm against the well-characterized data having the known profile, appropriate cutoffs or threshold values can be established by which calls can be made on values generated from using the algorithm on experimental or other unknown datasets to make predictions as to whether proteins being examined are likely to be part of a protein complex.

Thus the present invention identifies proteins with similar profiles, such as clusters of similar profiles, to identify or infer proteins that might be in a complex. Another approach is to start with a protein that is a known member of a complex, and compare the profile of this protein (e.g., intensity profile, as described above) with other proteins to find similar profiles inferring proteins that might be associated with the known protein in the complex. Further, the similarity measures described can be used to find de novo one or more groups of proteins that appear to belong in one or more clusters. Accordingly, the present techniques do not need to rely upon having prior knowledge of canonical profiles, such as profiles that define a pattern expected for a particular cellular location.

Figure 8:
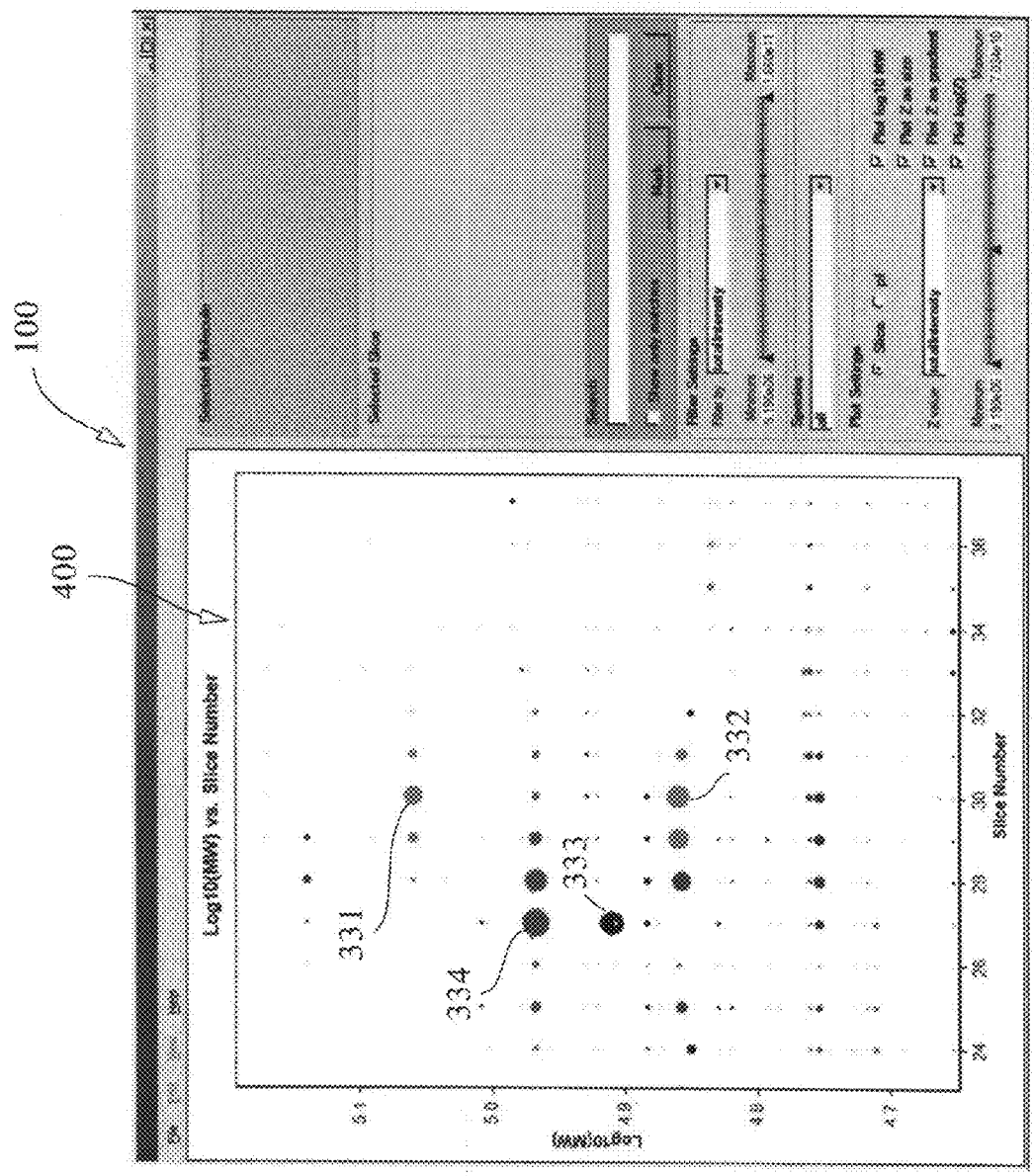
FIG. 8 illustrates plots having aligned coordinates that are overlaid and displayed simultaneously.

User interface 100 also provides the user the ability to visually compare multiple plots 200. By aligning coordinates of the X- and Y-axes of each plot 200 as displayed on the user interface, the system displays a plot 400, shown in FIG. 8, that represents molecular weight data values with different types of visual indicators depending upon whether that particular molecular weight value occurs in the first plot only, the second plot only, or in both plots. Of course, if the particular molecular weight value occurs in neither, then no visual representation is displayed at the X- and Y-coordinates for that particular molecular weight value. For example, in FIG. 8, data values for the first plot are represented by a first color (red, in the example shown), and data values for the second plot are represented by a second color (green, in this example). Indicator 331, which is colored red in this example, indicates that the $\log_{10}$ molecular weight data value of about 5.50 in slice number 30 occurs only in the first plot. Likewise, indicator 332, which is colored green in this example, indicates that the $\log_{10}$ molecular weight data value of about 4.86 in slice number 30 occurs only in the second plot.

If the mass occurs equally in both plots then that value is indicated by an indicator having a third color, in this example, black, as shown at 333. The intensities of the colors used for the first and second colors are proportional to the relative ratios of the mass in the first and second plots. This type of color mapping is accomplished by computing ratios of the abundances or total intensities of the overlying mass data values at a particular location and generating color gradients to represent those ratios. For example, indicator 334 is colored as a drab green shade, indicating that the mass occurs in both plots, but more abundantly in the second plot.

Alternative or in addition to the use of colors to distinguish the mass data values as occurring in the first, second, or both plots, other distinct indicators, such as unique geometrical representation, or other unique visual indicators, may be used.

Figure 9:
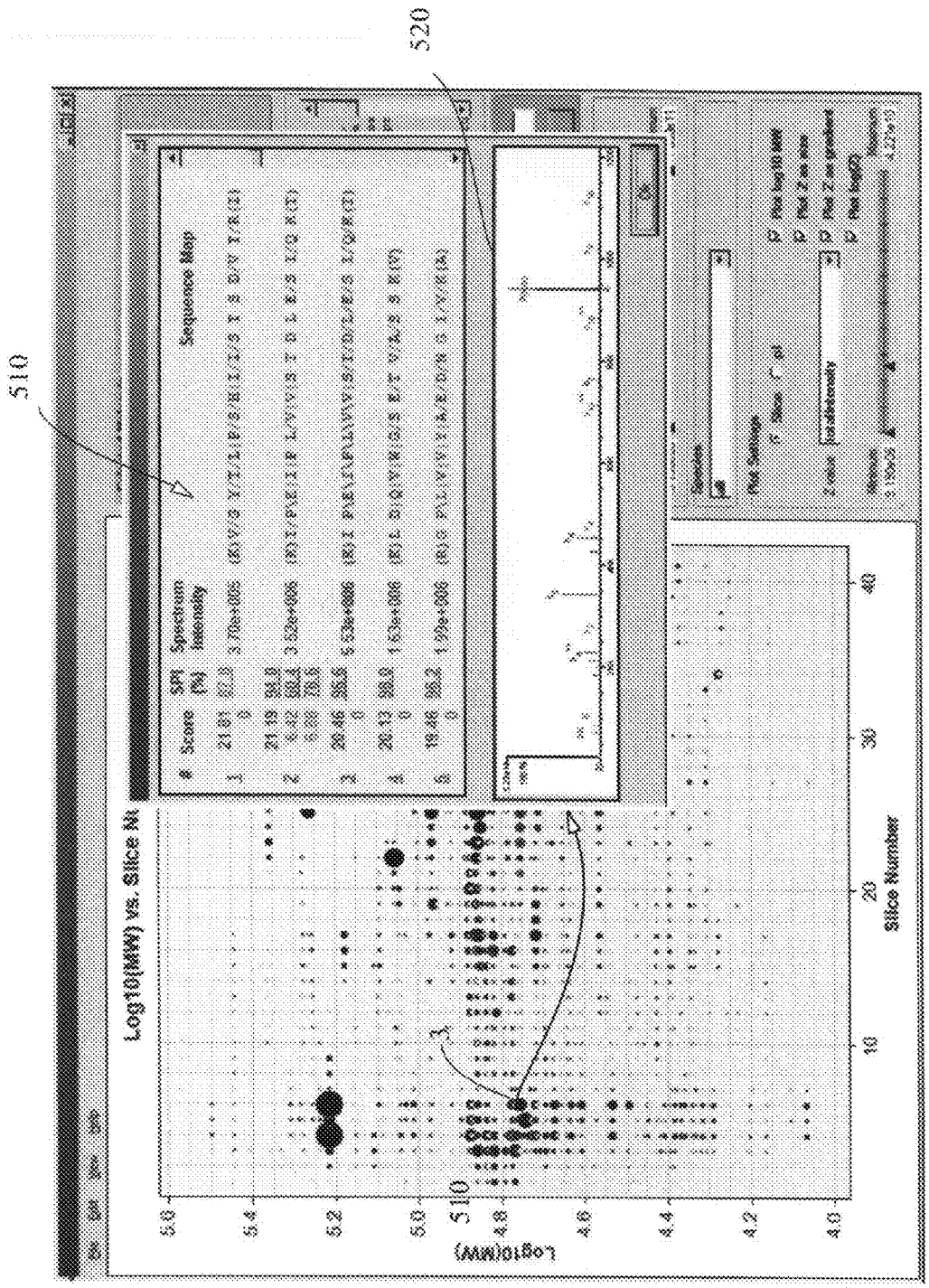
FIG. 9 illustrates to display of the mass spectrum data for a molecule represented by a selected mass data value on the plot.

As an additional optional feature, user interface 100 can be configured to plot associated mass spectrum data alongside plot 200 and/or partially overlaying plot 200. For example, if a user is particularly interested in a molecule represented by one or more mass data values on plot 200, the user can select a mass data value 3 in a manner described above. In the example of FIG. 9, the user has selected a specific protein (mass data value 3) from slice number 6. Further, the user may double click on the selected mass data value 3, or use some other mechanism to invoke the display of the mass spectrum data for that molecule and particular slice, as illustrated in FIG. 9. The mass spectrum data is obtained from the source data 22, as it is linked with the system via user interface 100. In the example of FIG. 9, the dialog pane 510 shows individual peptides associated with the selected protein (represented at mass data value indicated by indicator 3), as determined by the Spectrum Mill software. Pane 520 displays the MS spectrum of a peptide shown in the dialog pane 510 that was selected by the user to display its MS spectrum (in this example, peptide #1 was selected). The blue arrow shown in FIG. 9 is not generated by the software used to produce the visualization of FIG. 9, but has been placed on FIG. 9 to clarify which indicator 3 the user selected to display the MS data in pane 510. Of course the data displayed in pane 520 is also derivative of the same.

The present invention is not limited to the display and exploration of mass data values identified in gel slices as described above, but may be used for exploration of other data representing molecules existent in other types of portions (e.g., other slices, fractions, bins of a sample representing a physical separation of the molecules across different locations within the sample, etc.). For example, sub-cellular fractionation techniques are currently performed to enrich and analyze intracellular organelles for the study of protein complexes existent therein. In these instances, subsamples or fractions of the original sample can be separated (usually by ultracentrifugation) that are particular to different organelles or sub-cellular locations containing single proteins and protein complexes. Mass data values of the individual proteins in each portion can be plotted against the sub-cellular location or particular organelle (i.e., the corresponding portion).

In the case of sub-cellular fractionation, portions (i.e., fractions) do not correspond to a molecular weight range, but rather to a cellular location. Since the fractionation techniques used are not 100% accurate, it is useful to see the overlap of molecules between fractions ("portions"). This can serve as a diagnostic indicator of the quality of separation of the proteins that was achieved by the sub-cellular fractionation technique. Some proteins exist in more than one location (e.g., signaling and transport related proteins). Thus viewing the protein distribution across subcellular location can be informative regarding protein function, since the location or locations of a protein or protein complex can imply a great deal about the cellular function of the same.

An exemplary description of a sub-cellular fractionation process follows. Note that this is only one particular technique and that other techniques and variations of this technique are known in the art, and the present invention is not limited to any one particular technique. In this example, cells are lysed and subcellular components are separated by a series of centrifugations at increasing speeds. Following each centrifugation, the fraction of the sample that has sedimented to the bottom of the tube is recovered, and then further processed as a portion (fraction) in a manner as described above. The supernatant is then recentrifuged at higher speed to sediment the fraction. By repeatedly recovering the sedimented fractions and then re-centrifuging at a higher speed, a series of subsamples are provided, each enriched for different cellular locations. Each extracted sediment subsample thus is analogous to a "slice" as described above, and molecular weight data can be plotted against these sediment samples and processed and displayed in the manners described above. Each subsample thus does directly not correspond to an X,Y coordinate of a dimension of the sample or even a range of X,Y coordinates, but rather a cellular location within the sample that may include organelles.

Figure 10:
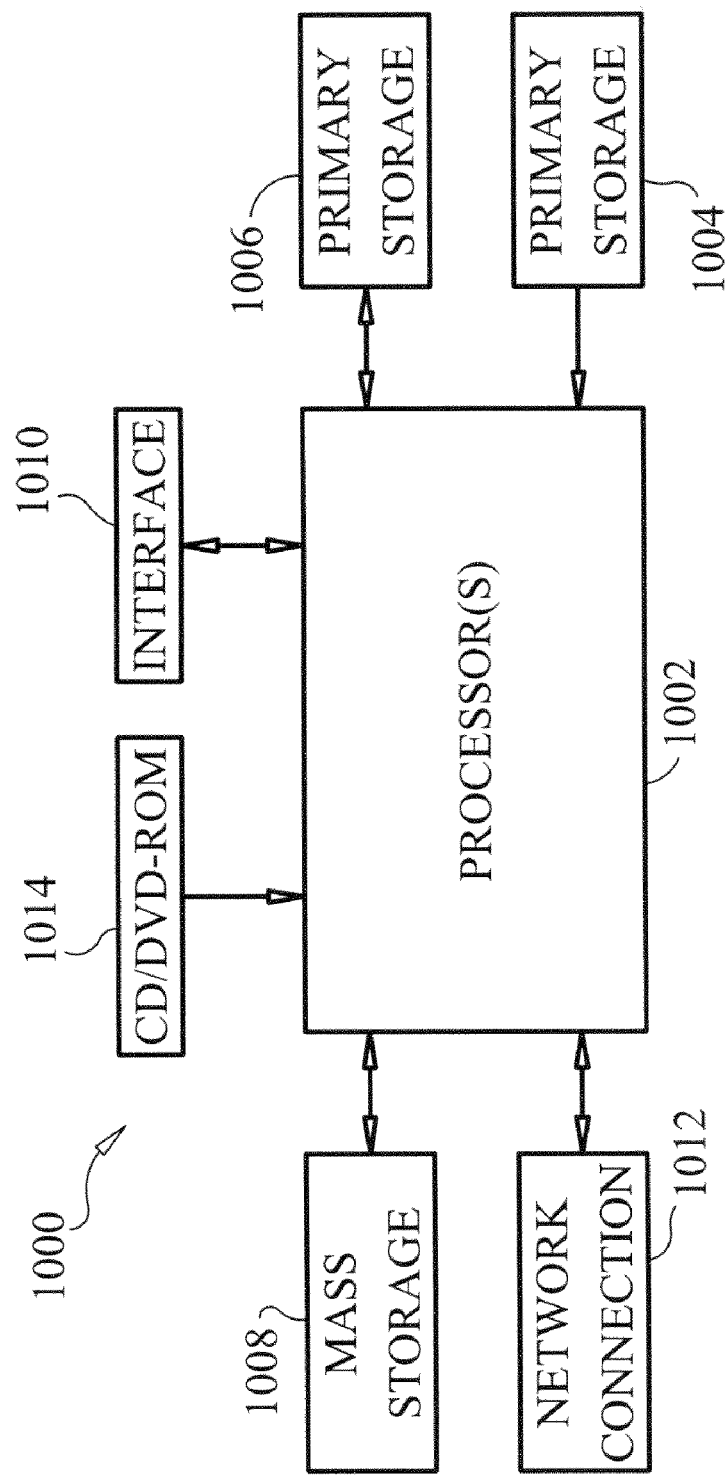
FIG. 10 illustrates a typical computer system in accordance with an embodiment of the present invention.

FIG. 10 illustrates a typical computer system 1000 in accordance with an embodiment of the present invention. The computer system 1000 may be incorporated into a system as described includes mass spectrometry hardware and software 18 and data analysis software tools 20, as well as user interface 100, user interface 100 may be incorporated into a computer system 1000 together with data analysis software tools 20, or user interface 100 may be incorporated into computer system 1000 and configured to receive data 22 as described in the processes herein, via interface 1010, for example, and with user interaction via user interface 100 that may be included as one of the interfaces 1010 of the system 1000. Computer system 1000 includes any number of processors 1002 (also referred to as central processing units, or CPUs) that are coupled to storage devices including primary storage 1006 (typically a random access memory, or RAM), primary storage 1004 (typically a read only memory, or ROM). Primary storage 1004 acts to transfer data and instructions unidirectionally to the CPU and primary storage 1006 is used typically to transfer data and instructions in a bi-directional manner. Both of these primary storage devices may include any suitable computer-readable media such as those described above.

A mass storage device 1008 is also coupled bi-directionally to CPU 1002 and provides additional data storage capacity and may include any of the computer-readable media described above. Mass storage device 1008 may be used to store programs, such as plotting programs, programs for filtering the mass data with input from user interface 100, etc. and is typically a secondary storage medium such as a hard disk that is slower than primary storage. It will be appreciated that the information from primary storage 1006, may, in appropriate cases, be stored on mass storage device 1008 as virtual memory to free up space on primary storage 1006, thereby increasing the effective memory of primary storage 1006. A specific mass storage device such as a CD-ROM or DVD-ROM 1014 may also pass data uni-directionally to the CPU.

CPU 1002 is also coupled to an interface 1010 that includes one or more input/output devices such as video monitors, user interface 100, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 1002 optionally may be coupled to a computer or telecommunications network using a network connection as shown generally at 1012. With such a network connection, it is contemplated that the CPU might receive information from the network, or might output information to the network in the course of performing the above-described method steps. The above-described devices and materials are known in the computer hardware and software arts.

The hardware elements described above may operate in response to the instructions of multiple software modules for performing the operations of this invention. For example, instructions for filtering and plotting methods and settings may be stored on mass storage device 1008 or 1014 and executed on CPU 1008 in conjunction with primary memory 1006.

While the present invention has been described with reference to the specific embodiments thereof, it should be understood that various changes may be made and equivalents may be substituted without departing from the scope of the invention defined by the claims. All such modifications are intended to be within the scope of the claims appended hereto.

We claim:

1. A method of visualizing data to facilitate analysis of the data, said method comprising:

providing mass data values for a sample having been separated into portions according to a first characteristic of the sample, the portions having been processed to provide the mass data values of members of the sample occurring in the portions;

displaying a plot of the mass data values on a first axis versus the portions on a second axis;

receiving a user input and selecting one of said mass data values of a member on the plot according to the user input; and displaying all mass data values occurring in the portion in which the selected mass data value is located using first visual indicators that are visibly distinct from visual indicators used to display data values occurring outside of the portion in which the selected data value is located.

2. The method of claim 1, further comprising:

displaying the selected mass data value using a second visual indicator that is visibly distinct from said first visual indicators and from visual indicators used to display mass data values not indicated by said first visual indicators; and displaying all other mass data values representing said member with said second visual indicator.

3. The method of claim 2, further comprising:

searching metadata characterizations of mass data values having been plotted, based upon a query input by a user;

identifying all instances of said metadata characterizations meeting requirements of said query; and indicating all occurrences of said mass data values corresponding to said metadata characterizations having been identified, with a third visual indicator that is visibly distinct from said first and second visual indicators and from visual indicators used to display mass data values not indicated by any of said first, second and third visual indicators.

4. The method of claim 3, further comprising displaying, adjacent said plot, a user interactive search pane at which a user can input said query, wherein said search pane is at least partially color coded to match a color coding of said third visual indicators.

5. The method of claim 1, further comprising displaying metadata characterizations of the member corresponding to the selected mass data value, in addition to displaying said plot.

6. The method of claim 5, wherein said metadata characterizations are displayed in a pane adjacent said plot and said pane is colored coded to match a color coding of the selected mass data value.

7. The method of claim 1, further comprising displaying metadata characterizations of said all mass data values occurring in the portion in which the selected mass data value is located, in addition to displaying said plot.

8. The method of claim 7, wherein said metadata characterizations are displayed in a pane adjacent said plot and said pane is colored coded to match a color coding of the first visual indicators.

9. The method of claim 1, further comprising indicating each of said mass data values proportionally to numeric data values corresponding to said mass data values.

10. The method of claim 9, wherein said numeric data values are intensity values.

11. The method of claim 1, further comprising filtering said mass data values based on a characteristic of said mass data values, and displaying a subset of the mass data values resulting from said filtering.

12. The method of claim 1, wherein said mass data values are provided from a sample separated by 1-D electrophoresis gel separation and said portions are gel slices.

13. The method of claim 1, wherein said mass data values are provided from a sample separated by sub-cellular fractionation, and said portions contain members located in sub-cellular locations different from members and sub-cellular locations of others of said portions.

14. The method of claim 1, further comprising:

plotting the mass data values on the first axis, versus pI values on the second axis.

15. The method of claim 1, further comprising:

selecting a mass data value representing a member, wherein the member is represented by mass data values in at least two contiguous portions;

comparing all mass data values representing said member along a chain of contiguous mass data values representing said member in which said mass data value having been selected is included, with all other members occurring in a same portion in which said mass data value having been selected occurs, and which include at least one additional mass data value occurring in a contiguous portion; and identifying those of said members that have a profile of a comparison characteristic, over contiguous mass data values thereof, similar to a profile of the comparison characteristic of the mass data value having been selected and its contiguous data values.

16. The method of claim 1, wherein said portions have processed by mass spectrometry to provide said mass data values, said method further comprising:

receiving user input invoking display of a mass spectrum data for said selected mass data value;

obtaining said mass spectrum data for said member corresponding to said selected mass data value; and displaying said mass spectrum data for said member adjacent said plot.

17. The method of claim 16, wherein said displaying said mass spectrum data comprises displaying a mass spectrograph.

18. A method of visualizing data to facilitate analysis of the data, said method comprising:

providing first mass data values for a first sample having been separated into first portions according to a first characteristic of the first sample, the first portions having been processed to provide the first mass data values of members of the first sample occurring in the first portions;

displaying a first plot of the first mass data values on a first axis versus the first portions on a second axis;

providing second mass data values for a second sample having been separated into second portions according to the first characteristic of the second sample, the second portions having been processed to provide the second mass data values of members of the second sample occurring in the second portions;

displaying a second plot of the second mass data values on a first axis versus the second portions on a second axis; and comparing at least one first mass data value in said first plot with at least one second mass data value in said second plot by:

receiving a user input and selecting one of said mass data values of member on the first or second plot according to the user input; and displaying all mass data values occurring in the portion in which the selected mass data value is located using first visual indicators that are visibly distinct from visual indicators used to display data values occurring outside of the portion in which the selected data value is located.

19. The method of claim 18, wherein said comparing comprises:
aligning coordinates of said first and second axes of said first plot, relative to a display with coordinates of said first and second axes of said second plot relative to said display; said method further comprising:
displaying mass data values occurring in both of said first and second plots using first visual indicators;
displaying mass data values occurring in said first plot but not in said second plots using second visual indicators, wherein said second visual indicator are distinct from said first visual indicators; and
displaying mass data values occurring in said second plot but not said first plot using third visual indicators, wherein said third visual indicator are distinct from said first and second visual indicators.

20. The method of claim 19, wherein the first visual indicators comprise a first color, the second visual indicators comprise a second color, and the third visual indicators comprise a third color, and wherein shading of said second and third colors varies according to relative to numerical values of the mass data values represented in said first and second plots.

21. A user interface for visualizing data and facilitating analysis of the data, the user interface comprising:
a display;
programming configured for receiving mass data values for a sample having been separated into portions according to a first characteristic of the sample, the portions having been processed to provide said mass data values of members of the sample occurring in the portions, and displaying a plot of the mass data values on a first axis versus the portions on a second axis;
a user selectable feature for selecting a data value of a member on the plot, wherein all mass data values occurring in the portion in which the selected mass data value is located are displayed using first visual indicators that are visibly distinct from visual indicators used to display mass data values occurring outside of the portion in which the selected mass data value is located.

22. The user interface of claim 21, wherein the selected mass data value is displayed using a second visual indicator that is visibly distinct from said first visual indicators and from visual indicators used to display mass data values not indicated by said first indicator or said second indicator; and wherein all other mass data values representing said member are displayed using said second visual indicator.

23. The user interface of claim 21, further comprising a pane configured to display, adjacent to said plot, metadata characterizations of the member corresponding to the selected mass data value.

24. The user interface of claim 21, further comprising a pane configured to display metadata characterizations corresponding to said selected mass data value, and wherein at least a portion of said pane is colored coded to match a color coding of the selected mass data value.

25. The user interface of claim 21, further comprising a pane configured to display, adjacent to said plot, metadata characterizations of said all mass data values occurring in the portion in which the selected mass data value is located.

26. The user interface of claim 21, further comprising a user interactive feature for searching metadata characterizations of mass data values having been plotted, based upon a query inputted by the user.

27. The user interface of claim 21, further comprising a user interactive feature for filtering said mass data values based on a characteristic of said mass data values, and displaying a subset of the mass data values resulting from said filtering.

28. The user interface of claim 21, wherein said portions have processed by mass spectrometry to provide said mass data values, said user interface further comprising:
a user interactive feature for invoking display of mass spectrum data for said selected mass data value;
programming for obtaining mass spectrum data for said member corresponding to said selected mass data value, from data produced by said mass spectrometry; and
displaying a mass spectrograph for said member adjacent said plot.

29. A non-transitory computer readable storage medium carrying one or more sequences of instructions for visualizing data and facilitating analysis of the data, wherein execution of the one or more sequences of instructions by one or more processors causes the one or more processors to perform a process comprising: receiving mass data values for a sample having been separated into portions according to a first characteristic of the sample, the portions having been processed to provide the mass data values of members of the sample occurring in the portions; displaying a plot of the mass data values on a first axis versus the portions on a second axis; receiving a user input and selecting a mass data value of a member on the plot according the user input; and displaying all mass data values occurring in the portion in which the selected data value is located using first visual indicators that are visibly distinct from visual indicators used to display data values occurring outside of the portion in which the selected data value is located.

30. A non-transitory computer readable storage medium carrying one or more sequences of instructions for visualizing data and facilitating analysis of the data, wherein execution of the one or more sequences of instructions by one or more processors causes the one or more processors to perform a process comprising: receiving first mass data values from a first sample having been separated into first portions according to a first characteristic of the first sample, the first portions having been processed to provide the first mass data values of members of the first sample occurring in the first portions; displaying a first plot of the first mass data values on a first axis versus the first portions on a second axis; receiving second mass data values for a second sample having been separated into second portions according to the first characteristic of the second sample, the second portions having been processed to provide the second mass data values of members of the second sample occurring in the second portions; displaying a second plot of the second mass data values on a first axis versus the second portions on a second axis; and comparing at least one first mass data value in said first plot with at least one second mass data value in said second plot by receiving a user input and selecting one of said mass data values of member on the first or second plot according to the user input; and displaying all mass data values occurring in the portion in which the selected mass data value is located using first visual indicators that are visibly distinct from visual indicators used to display data values occurring outside of the portion in which the selected data value is located.

* * * * *